United States Patent [19]

Collington et al.

[11] 4,327,092
[45] Apr. 27, 1982

[54] AMINOCYCLOPENTANE ALKENOIC ACIDS AND ESTERS AND PHARMACEUTICAL FORMULATIONS

[75] Inventors: Eric W. Collington, Welwyn; Peter Hallett, Buntingford; Christopher J. Wallis, Royston, all of England

[73] Assignee: Glaxo Group Limited, England

[21] Appl. No.: 258,737

[22] Filed: Apr. 29, 1981

[30] Foreign Application Priority Data

Jan. 7, 1981 [GB] United Kingdom ............... 00326/81

[51] Int. Cl.³ ............... C07D 413/12; A61K 31/535; A61K 31/54; C07D 417/12
[52] U.S. Cl. .............................. 424/246; 424/45; 424/248.51; 424/248.53; 424/248.55; 424/250; 424/267; 424/274; 424/275; 424/285; 544/58.2; 544/58.7; 544/146; 544/152; 544/379; 546/213; 546/214; 542/426; 260/326.35; 260/326.36; 260/330.3; 260/347.3; 260/347.4
[58] Field of Search ........... 260/330.3, 326.35, 326.36, 260/347.3, 347.4; 544/146, 152, 58.2, 58.7, 379; 546/213, 214; 542/426; 424/45, 246, 248.51, 248.53, 248.55, 250, 267, 274, 275, 285

[56] References Cited

U.S. PATENT DOCUMENTS

| | | | |
|---|---|---|---|
| 4,182,903 | 1/1980 | Favara et al. | 562/503 |
| 4,189,606 | 2/1980 | Favara et al. | 562/455 |
| 4,239,778 | 12/1980 | Venton et al. | 424/305 |
| 4,265,891 | 5/1981 | Collington et al. | 424/244 |

FOREIGN PATENT DOCUMENTS

2705797 9/1977 Fed. Rep. of Germany .
2028805 3/1980 United Kingdom .

OTHER PUBLICATIONS

Enke et al., Abstract Papers of the American Chemical Society, 176th Meeting, MEDI 28 (1978).
Orth et al., Topics in Current Chemistry, 72, 51–97 (1977).

Primary Examiner—Henry R. Jiles
Assistant Examiner—R. W. Ramsuer
Attorney, Agent, or Firm—Bernard, Rothwell & Brown

[57] ABSTRACT

Compounds are described of the formula

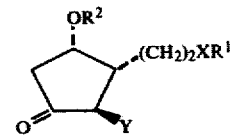

(and their salts and solvates) in which:
X is cis or trans —CH=CH—;
$R^1$ is $C_{1-7}$ alkyl terminated by —COOR³ where $R^3$ is H, $C_{1-6}$ alkyl or $C_{7-10}$ aralkyl;
Y is a saturated heterocyclic amino group having 5–8 ring members; and
$R^2$ is substituted or unsubstituted thienylalkyl or furanylalkyl.

These compounds inhibit blood platelet aggregation and bronchoconstriction and may be formulated for use as antithrombotic and anti-asthmatic agents.

8 Claims, No Drawings

AMINOCYCLOPENTANE ALKENOIC ACIDS AND ESTERS AND PHARMACEUTICAL FORMULATIONS

The endoperoxides prostaglandins G$_2$ and H$_2$, and thromboxane A$_2$ are naturally occurring, reactive metabolites of arachidonic acid in human platelets. They are not only potent aggregatory agents but are also constrictors of vascular and bronchial smooth muscle, and therefore substances which antagonise their effects are of considerable interest in human medicine.

We have now found a new group of compounds which have shown endoperoxide and thromboxane antagonist activity, and are therefore of interest in the treatment of asthma and cardiovascular diseases. These compounds can broadly be described as cyclopentanealkenoic acids and esters in which the double bond is in the 3,4-position in relation to the cyclopentane ring and in which the ring is substituted by heterocyclic amino, oxo and heterocyclic aralkoxy groups.

The invention thus provides compounds of the general formula (1)

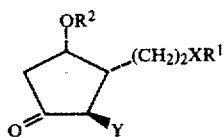

(1)

wherein

X is cis or trans —CH=CH—;

R$^1$ is straight or branched C$_{1-7}$ alkyl bearing as a terminal substituent —COOR$^3$ where R$^3$ is a hydrogen atom, C$_{1-6}$ alkyl or C$_{7-10}$ aralkyl (e.g. benzyl);

Y represents a saturated heterocyclic amino group which has 5-8 ring members and (a) optionally contains in the ring —O—, —S—, —SO$_2$—, —NR$^4$ (where R$^4$ is a hydrogen atom, C$_{1-7}$ alkyl or aralkyl having a C$_{1-4}$ alkyl portion);

and/or (b) is optionally substituted by one or more C$_{1-4}$ alkyl groups;

R$^2$ is C$_{1-5}$ alkyl substituted by thienyl or furanyl [the thienyl and furanyl groups being optionally substituted by C$_{1-6}$ alkyl, C$_{1-6}$ alkoxy, aryl (e.g. phenyl) or phenyl (C$_{1-3}$) alkyl or phenyl (C$_{1-3}$)-alkoxy (the aryl or phenyl group in each case being optionally substituted by C$_{1-3}$ alkyl, C$_{1-3}$ alkoxy or halogen), aryloxy (e.g. phenoxy), C$_{5-7}$ cycloalkyl, halogen, nitro or thienyl];

and the physiologically acceptable salts and the solvates (e.g. hydrates) thereof.

The structural formulae herein are to be understood to include the enantiomers of each of the compounds concerned as well as mixtures of the enantiomers, including racemates, even though the precise structure as set out only relates to one enantiomer.

The alkyl groups referred to above in the definition of the compounds of formula (1) may be straight or branched.

The alkyl portion of the group R$^1$ may for example contain 1-5 carbon atoms, in a straight or branched chain, and is preferably —CH$_2$CH$_2$—. Examples of suitable R$^3$ groups are C$_{1-3}$ alkyl (e.g. methyl), but R$^3$ is preferably a hydrogen atom. R$^1$ is thus preferably —(CH$_2$)$_2$COOH.

When R$^3$ is a hydrogen atom, the compounds are capable of salt formation with bases and the compounds are preferably used in the form of such salts. Examples of suitable salts are alkali metal (e.g. sodium and potassium), alkaline earth metal (e.g. calcium or magnesium), ammonium, substituted ammonium (e.g. tromethamine or dimethylaminoethanol), piperazine, N,N-dimethylpiperazine, morpholine, piperidine and tertiary amino (e.g. triethylamine) salts. Inorganic salts are preferred.

X is preferably a cis —CH=CH— group.

The heterocyclic amino group Y may for example have a 5, 6 or 7-membered ring, e.g. pyrrolidino, piperidino, morpholino, piperazino, thiamorpholino, 1-dioxothiamorpholino, homomorpholino and hexamethyleneimino. Examples of the optional substituents which may be present on a second nitrogen atom in the ring are methyl, ethyl and benzyl. The carbon atoms of the heterocyclic rings may for example be substituted by methyl or ethyl. Y is preferably piperidino, morpholino, homomorpholino, thiamorpholino or 1-dioxothiamorpholino, and compounds in which Y is a morpholino or piperidino groups are particularly preferred.

The amino group Y enables the compounds to form salts with organic acids, e.g. maleates.

R$^2$ may for example be C$_{1-5}$ alkyl (e.g. methyl or propyl) substituted by furanyl or thienyl (optionally substituted by a phenyl group).

R$^2$ is preferably thienylalkyl in which the alkyl portion contains 1-3 carbon atoms and the thienyl group is substituted by a phenyl group. Particularly preferred R$^2$ groups are thienylmethyl (particularly a 4-thienylmethyl group) substituted by a phenyl group, which substituent is preferably in the 2-position.

A particularly preferred group of compounds has the formula (1) in which:

X is cis —CH=CH—,

R$^1$ is —CH$_2$CH$_2$COOH,

Y is morpholino or piperidino, and

R$^2$ is phenylthienylmethyl;

and the physiologically acceptable salts and solvates (e.g. hydrates) thereof.

A particularly important compound in this latter group is that in which Y is morpholino and R$^2$ is 2-phenylthien-4-ylmethyl.

In general, compounds of formula (1) in which the carbon atom carrying the —(CH$_2$)$_2$XR$^1$ group is in the R-configuration (and mixtures containing this isomer) are preferred.

Compounds of formula (1) inhibit blood platelet aggregation and bronchoconstriction. The test for inhibition of platelet aggregation is as described by G. V. Born in Nature 194, 927-929 (1962) except in that collagen is used instead of ADP as the pro-aggregatory agent. The test for potential inhibition of bronchoconstriction is as described by K. M. Lulich et al. in British Journal of Pharmacology 58, 71-79 (1976) except guinea-pig lung is used instead of cat lung.

The compounds are thus of interest in the treatment of asthma, and as inhibitors of platelet aggregation and thrombosis for use in renal dialysis and the treatment and prevention of occlusive vascular diseases such as arteriosclerosis, atherosclerosis, peripheral vascular disease, cerebral vascular disease including transient ischaemic attacks, stroke, plumonary embolism, diabetic retinopathy, post operative thrombosis, angina and myocardial infarction. They may be formulated in conventional manner for use, with one or more pharmaceutical carriers.

For oral administration, the pharmaceutical composition may take the form of, for example, tablets, capsules, powders, solutions, syrups, or suspensions prepared by conventional means with acceptable excipients.

The compounds may be formulated for parenteral administration by bolus injections or continuous infusion. Formulations for injections may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution before use with a suitable vehicle, e.g. sterile pyrogen-free water.

For administration by inhalation the compounds are conveniently delivered in the form of an aerosol spray presentation from pressurized packs or a nebuliser, or as a cartridge from which the powdered composition may be inhaled with the aid of a suitable device. In the case of a pressurized aerosol the dosage unit may be determined by providing a valve to deliver a metered amount.

For use as antithrombotic agents, the compounds are preferably administered orally, for example in amounts of 0.05 to 10 mg/kg body weight, 1 to 4 times daily.

For use in the treatment of asthma, the compounds may also be administered orally in amounts of 0.05 to 10 mg/kg body weight, 1 to 4 times daily; preferably however they are administered by inhalation at doses varying from 0.3 to 30 mg, 1 to 4 times daily. The compounds may be used in combination with other antiasthmatic agents.

The precise dose administered will of course depend on the age and condition of the patent.

Suitable methods for preparing compounds of formula (1) are described below.

In the following discussion, the groups $R^1$, $R^2$, $R^3$, X and Y are as defined above except where otherwise indicated.

(a) Compounds of formula (1) may be prepared by oxidising a corresponding hydroxy compound, e.g. a compound of formula (2)

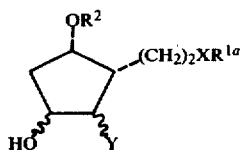

(2)

(wherein $R^{1a}$ is $C_{1-7}$ alkyl substituted by —COOR$^3$, —CH$_2$OH or —CHO).

Suitable methods of oxidation include using a Cr$^{VI}$ oxidising reagent in a suitable solvent, e.g. chromic acid in acetone (e.g. Jones reagent, preferably used in the presence of a diatomaceous silica such as Celite) or CrO$_3$ in pyridine. These reagents are for example used at temperatures of $-20°$ to room temperature.

Other important methods include using an activated sulphur reagent, e.g. (i) N-chlorosuccinimidedimethylsulphide complex in a suitable solvent (e.g. toluene or dichloromethane) at temperatures of for example $-25°$ to 25°, preferably at 0°-5°, (ii) a dimethylsulphide (e.g. dimethylsulphoxide) activated by a suitable electrophilic reagent (such as oxalyl chloride, acetyl bromide or thionyl chloride) in a suitable solvent (e.g. toluene or dichloromethane), e.g. at $-70°$ to $-20°$; dicyclohexylcarbodiimide can also be used as the electrophilic reagent (preferably in the presence of CF$_3$COOH or its pyridinium salt) at for example $-10°$ to room temperature, using the same solvents, or (iii) pyridine —SO$_3$ complex in dimethylsulphoxide, preferably at 0° to room temperature.

When $R^3$ is a hydrogen atom, better yields are sometimes obtained by prior protection of the carboxyl group, for example in the form of a trialkyl (e.g. trimethyl, triethyl or dimethyl (1,1-dimethylethyl))silyl ester.

Cr$^{VI}$ oxidising agents are generally preferred. The choice of oxidation method however will depend on the nature of the starting material of formula (2). Thus when $R^{1a}$ is —CH$_2$OH or —CHO, a Cr$^{VI}$ oxidising agent will generally be used. When Y is in the $\alpha$-configuration conditions should be chosen to effect epimerisation, either at the same time or after oxidation.

Any hydroxy or amino group present in the starting material and required in the end product should be suitably protected in this reaction.

(b) Compounds of formula (1) in which $R^3$ is an alkyl or aralkyl group can be prepared by esterification of the corresponding carboxylic acid in which $R^3$ is a hydrogen atom, reaction with a diazoalkqne being preferred.

Alternatively, the acid may be converted into an activated derivative (e.g. a corresponding mixed anhydride) e.g. by reaction with an alkyl chloroformate (e.g. isobutyl chloroformate) in the presence of a suitable base, e.g. triethylamine or pyridine. The activated derivative can then be reacted with an appropriate alcohol, for example using a solvent such as acetone and temperature of $-10°$ to room temperature.

(d) Compounds of formula (1) may also be prepared by selective reduction of a corresponding compound of formula (1) in which X is an acetylene group. These intermediates are also novel compounds. Suitable methods of reduction include using hydrogen in the presence of a catalyst, e.g. palladium on a support (e.g. CaCO$_3$ or BaSO$_4$) and poisoned for example by lead or pyridine. Suitable solvents include ethyl acetate or methanol.

(e) Where salts of compounds of formula (1) are desired such salts may be formed by conventional methods, for example by treating acids of formula (1) with appropriate bases. Salts may also be formed with acids.

The salts may be formed in conventional manner. For example, amine salts are conveniently prepared by adding the amine to a solution of an acid of formula (1) in a solvent such as ether. Salts of inorganic bases may be prepared by adding the base to a solution of the acid in an aqueous organic solvent. Certain salts may also be prepared by exchange of cation; for example, calcium salts may be prepared by addition of a calcium salt (e.g. the chloride or acetate) to a solution of a salt of a compound of formula (1), e.g. an amine or alkali metal salt.

The principal intermediates required for the reactions described above may be prepared by the following methods.

It will be appreciated that the following reactions will frequently require the use of, or will conveniently be applied to, starting materials having protected functional groups. It is to be understood generally that the references below to specific starting materials are intended to include references to corresponding materials having protected functional groups.

It will also be appreciated that certain of the reactions described below are capable of affecting other groups in the starting material which are desired in the end product, and account must be taken of this when performing multi-stage reactions.

(f) Compounds of formula (3)

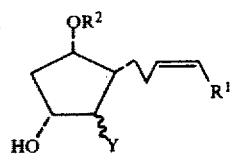

(where $R^1$ is as defined above for $R^1$ where $R^3$ is a hydrogen atom) may be prepared by reacting a compound of formula (4)

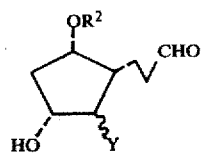

with an appropriate Wittig reagent, e.g. a phosporane of formula $R_3{}^7P=CHR^1$ (where $R^7$ is $C_{1-6}$ alkyl or aryl, e.g. monocyclic aryl such as phenyl) or a salt thereof, e.g. the potassium salt. Suitable reaction solvents include hydrocarbons (e.g. benzene and toluene), ethers (e.g. tetrahydrofuran), dialkylsulphoxides (e.g. dimethylsulphoxide), alcohols and halogenated hydrocarbons. The reaction may be carried out at any suitable temperature from $-70°$ to $50°$ C., preferably at room temperature.

The reaction is particularly suitable for the preparation of compounds in which $R^1$ is terminally substituted by —COOH (in salt form). Any hydroxy group present is preferably in a protected state prior to this reaction. Suitable hydroxyl protecting groups are described below. Any —NH$_2$ group present should also be protected, e.g. by t-butoxycarbonyl.

If desired, the configuration of the group X and $R^1$ and $R^2$ may then be modified to provide other compounds of formula (2) e.g. by methods (1)–(m) below or (b) above.

The starting materials of formula (4) may be prepared by the following sequence:

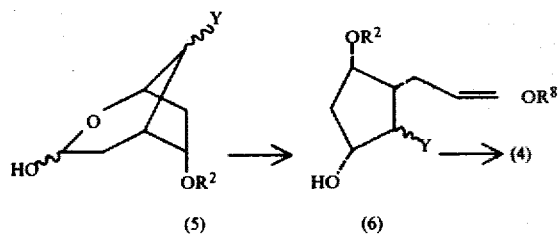

A lactol of formula (5) is treated with an appropriate Wittig reagent (e.g. $R_3{}^7P=CHOR^8$, where $R^7$ is as defined above and $R^8$ is $C_{1-4}$ alkyl) to give the vinyl ether (6). The reactions may be performed as described for process (f). The vinyl ether (6) is then hydrolysed to give the aldehyde (4), for example using a dilute acid such as hydrochloric acid. Acetone is a suitable solvent.

Lactols of the formula (7)

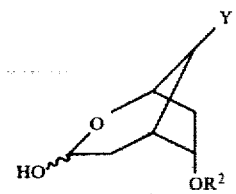

may be prepared by the method described in British Patent Specification No. 2028805A, using starting materials containing the appropriate $R^2$ group.

Lactols of formula (8)

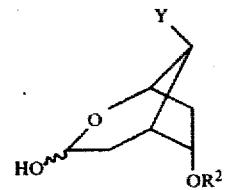

required as starting materials may be prepared by the following sequence:

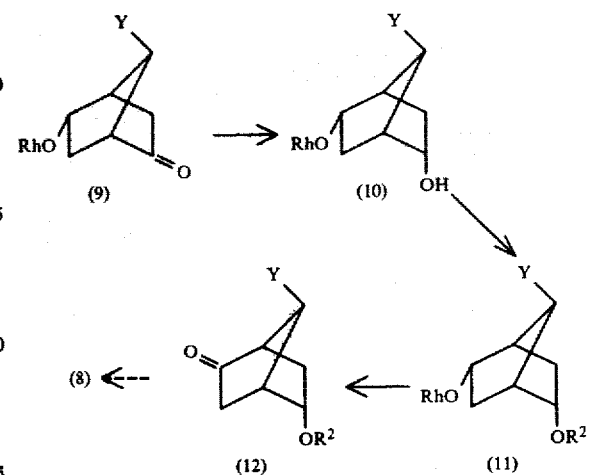

($R^h$ above represents a hydroxyl protecting group) Thus the norbornanone (9) is first reduced (e.g. with NaBH$_4$) to the alcohol (10) into which the $R^2$ group is then introduced (e.g. by reaction with $R^2L$, where L is a leaving group, e.g. halogen or tosylate) to give the compound (11). The protecting group ($R^h$) is then removed and the hydroxy group oxidised (e.g. as described for process (a) to give the norbornanone (12). The latter can then be converted into the lactol (8) by Baeyer-Villiger oxidation followed by reduction (e.g. with di-isobutyl aluminium hydride).

(g) Compounds of formula (2) in which the groups Y and OH are both in the $\beta$-position may be prepared by reducing the corresponding compound of formula (1), e.g. with lithium tri-sec-butyl borohydride.

(h) Compounds of formula (2) in which $R^{1a}$ contains —CH$_2$OH may be prepared by reducing the corresponding acid or ester of formula (2) or (1), e.g. with LiAlH$_4$.

(j) Compounds of formula (2) in which $R^{1a}$ contains —CHO may be prepared in the same manner as generally described for process (f) by reacting a compound of formula (4) with a phosphorane of formula $R_3^7P=CHR^{1a}$ in which $R^{1a}$ is $C_{1-7}$ alkyl substituted by a protected formyl group (e.g. acetal). Removal of the protecting group then gives the required formyl intermediate.

(k) Compounds of formula (2) in which Y is in the α-configuration and the ring hydroxy group is in the β-configuration may be prepared by epimerising the corresponding compound in which the ring hydroxy group is in the α-position. This may for example be effected with triphenylphosphine in the presence of an acid (e.g. formic or benzoic acid) and $(C_2H_5OOC.N)_2$ at a low temperature. Tetrahydrofuran is a suitable solvent.

(k) The acetylenes required as starting materials for process (d) may be prepared by first reacting a compound of formula (7) with a Wittig reagent $(R_3^7P=CBrR^1)$, as described above for process (f). The product is then dehydrobrominated to form the side chain acetylene group, and the ring hydroxy group then oxidised, as described for process (a).

(m) Compounds of formula (2) in which X is trans —CH=CH— may be prepared by isomerising the corresponding cis compound. The isomerisation may for example be effected by treatment with, for example, p-toluene sulphinic acid in dioxan (e.g. at reflux) or azobisisobutyronitrile and thiophenol, using for example a hydrocarbon solvent (e.g. benzene) and any suitable temperature up to reflux.

(q) Compounds of formula (3) in which Y is in the β-configuration may be prepared by etherification of the corresponding hydroxy compound in which $R^2$ is a hydrogen atom. The reaction may for example be performed with an appropriate reagent $R^2L$ (L is as defined above), for example by reaction at room temperature in the presence of a suitable base (e.g. sodium hydride) in a suitable solvent (e.g. dimethylformamide).

Any other hydroxy group present in the starting material used in process (q) should be protected in this reaction, as should the —COOH group in compounds in which $R^3$ is a hydrogen atom.

Suitable starting materials of formula (16) for possess (q) above may be prepared by the following sequence:

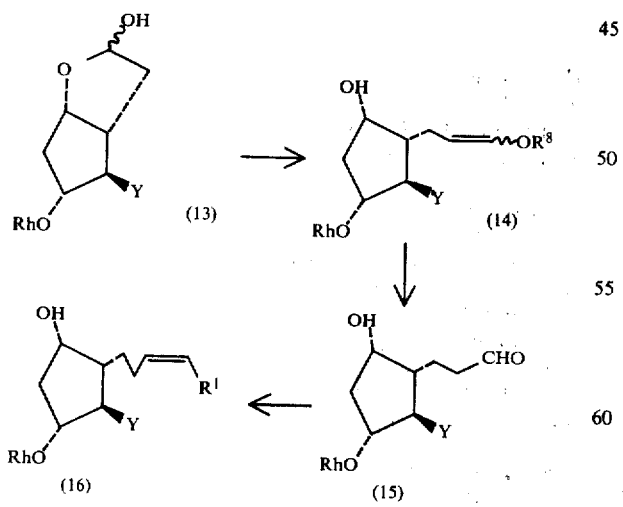

A lactol of formula (13), in which —$OR^h$ is a protected hydroxy group is first treated with a Wittig reagent to give the vinyl ether (14), which is then converted into the aldehyde (15) by treatment with mercuric acetate. These steps are performed in the same general way as for the preparation of compounds of formula (4). The compound of formula (16) may then be formed from the aldehyde (15) by the method of process (f).

The preparation of the lactols (13) is described in British Patent Specification No. 2028805A.

As an alternative to the formation of the ether group by process (q), it may be formed at an earlier stage, by etherification of the compound of formula (14). (s) Compounds of formula (2) may also be prepared by modifying the corresponding compound in which Y is —$NH_2$.

This reaction may be performed by treating the starting material with a compound of the formula $ZR^9Z$, where Z is a readily displaceable group (such as halo, e.g. iodo, or hydrocarbylsulphonyloxy, e.g. p-toluenesulphonyloxy) and $R^9$ is the appropriate divalent group (e.g. —$(CH_2)_2S(CH_2)_2$—). The reaction may be carried out in a solvent such as acetonitrile or methanol at reflux, in the presence of a suitable base, e.g. potassium carbonate or sodium bicarbonate.

The amines required as starting materials for process (s) may be prepared by reduction of the corresponding azide, for example using zinc and $NaH_2PO_4$ (e.g. in tetrahydrofuran).

The azide starting materials may be prepared by methods analogous to those for preparing the compounds of formula (3), using reagents in which Y is an azido group. In particular, the preparations of lactols of formula (7) in which Y is azido is described in British Patent Specification No. 2028805A.

If desired, modification of the group $R^1$ or the configuration of the double bond may be effected before the formation of the group Y by process (s). The amino group may need to be protected in such transformations.

In the preparation of the intermediates the ring hydroxy group will often be protected and the liberation of this (or any other hydroxy group present) will frequently be the last step in the preparation. Conventional methods of protection may be used, protection in the form of dimethyl-1,1-dimethylethyl-silyloxy or tetrahydropyranyloxy groups being preferred. These groups may be removed by acid hydrolysis. Hydroxy groups may also be protected in the form of alkanoyloxy groups having up to 7 carbon atoms, e.g. acetoxy. These groups may be removed by alkaline hydrolysis.

When a specific enantiomer of formula (1) is required, intermediates having the required stereochemical configuration should be used in the above processes. For example, enantiomeric bromohydrin (17)

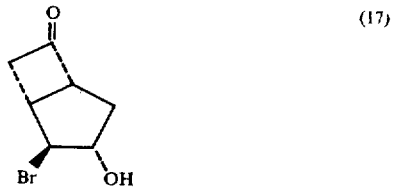

can be prepared by the method described by Newton et al in J.C.S. Chem. Comm., 1979, 908. This can then be converted into a compound of formula (1) in which the carbon atom carrying the —$(CH_2)_2XR^1$ group is in the (R)-configuration, via the appropriate enantiomer of the lactol (7), using the methods described above.

The following examples illustrate the invention. "Jones reagent" is a solution of chromic acid and sulphuric acid in water. A 2.67 M solution contains $CrO_3$ (26.7 g) and concentrated $H_2SO_4$ (23 ml) made up to 100 ml with water.

Temperatures are in °C. The following abbreviations are used:

TLC—thin layer chromatography using $SiO_2$;
PE—petroleum ether (boiling at 40°–60° unless otherwise stated);
DIBAL—diisobutylaluminium hydride;
THF—tetrahydrofuran;
DMF—dimethylformamide;
ER—ether;
EA—ethyl acetate;
DMSO—dimethylsulphoxide.

Chromatography was carried out using silica gel unless otherwise stated. 'Dried' refers to drying with $MgSO_4$. 'Hyflo' is a filtration aid.

INTERMEDIATE 1

(1α,2α,3β,4α)-(±)-2-(3-Methoxy-2-propenyl)-3-(4-morpholinyl)-4-[(tetrahydro-2H-pyran-2-yl)oxy]cyclopentanol, acetate (ester)

To a cold (0°) stirred solution of potassium tert-butoxide (2.15 g) in dry THF (40 ml) under nitrogen, was added portionwise (methoxymethyl)triphenyl phosphonium chloride (6.57 g). The suspension was stirred for 15 min., whereupon a solution of (3aα,-4α,5β,6aα)-hexahydro-4-(4-morpholinyl)-5-(tetrahydro-2H-pyran-2-yl)oxy-2H-cyclopenta(b)-furan-2-ol (2 g) in dry THF (30 ml) was added dropwise. Stirring was continued at room temperature for 1 h, when methanol (30 ml) was added followed by evaporation of the mixture to dryness. The residue was treated with acetic anhydride (8 ml) and pyridine (10 ml) and left for 40 h. Evaporation in vacuo gave a residue which was treated with 8% $NaHCO_3$ solution (50 ml) and extracted with $CH_2Cl_2$ (3×20 ml). The combined extracts were washed with brine (2×15 ml), dried and concentrated. Purification of the residue, initially by chromatography using 4:1 ER-methanol as eluent, and then by trituration with PE gave the title compound as an oil (13.23 g). IR (Neat) 1735, 1655 cm$^{-1}$

INTERMEDIATE 2

(1α,2α,3β,4α)-(±)-2-(3-Methoxy-2-propenyl)-3-(4-morpholinyl)-4-[(tetrahydro-2H-pyran-2-yl)oxy]cyclopentanol A solution of Intermediate 1 (0.3 g) in 0.5 N NaOH (10 ml) was left to stand for 10 min., then extracted with ER (3×20 ml). The combined extracts were dried, filtered and evaporated to given the title compound as an oil (0.25 g). IR (Neat) 3450, 1655 cm$^{-1}$.

INTERMEDIATE 3

(1α,2β,3β,5β)-(±)-4-[2-(3-Methoxy-2-propenyl)-3-(4-phenylthien-2-yl)methoxy]-5-[(tetrahydro-2H-pyran-2-yl)oxy]cyclopentyl]morpholine Prepared from Intermediates 2 and 10 using the method of Intermediate 6. Purification by chromatography using EA as eluent.

INTERMEDIATE 4

(1α,2β,3α,5α)-(±)-3-Hydroxy-2-(4-morpholinyl)-5-[(4-phenylthien-2-yl)methoxy]cyclopentanepropanal Prepared from Intermediate 3 using the method of Intermediate 7. Purification by chromatography using 9:1 ER-methanol as eluent. IR (CHBr$_3$) 3580–3540, 2720, 1718 cm$^{-1}$

INTERMEDIATE 5

[1α(Z),2β,3α,5α]-(±)-7-[3-Hydroxy-2-(4-morpholinyl)-5-[(4-phenylthien-2-yl)methoxy]cyclopentyl]-4-heptenoic acid Prepared from Intermediate 4 using the method of Intermediate 8.

INTERMEDIATE 6

(1α,2β,3β,5β)-(±)-4-[2-(3-Methoxy-2-propenyl)-3-[(2-phenylthien-4-yl)methoxy]-5-[(tetrahydro-2H-pyran-2-yl)oxy]cyclopentyl]morpholine NaH (0.952 g, 50% in oil) was added to a stirred solution of Intermediate 14 (5.38 g) and Intermediate 2 (2.6 g) in DMF (15 ml) at 0°. Stirring at room temperature was continued for 2h whereupon saturated $NH_4Cl$ solution (50 ml) was added and the mixture extracted with ER (3×50 ml). The combined extracts were washed with water (2×100 ml), brine (100 ml) and then dried. Evaporation gave an oil which was chromatographed on silica using 19:1 ER-methanol as eluent to give the title compound (2.87 g).

Analysis Found: C, 68.1; H, 7.8; N, 2.7. $C_{29}H_{38}NO_5S$ requires: C, 68.0; H, 7.4; N, 2.7%.

INTERMEDIATE 7

(1α,2β,3α,5α)-(±)-3-Hydroxy-2-(4-morpholinyl)-5-[(2-phenylthien-4-yl)methoxy]cyclopentanepropanal A solution of Intermediate 6 (2.75 g) in acetone (20 ml) was treated with 2 N hydrochloric acid (10 ml) for 2h. 2 N $Na_2CO_3$ solution (10 ml) was then added and the acetone removed in vacuo. The remaining solution was basified by adding more $Na_2CO_3$ solution and the mixture was extracted with ER (3×30 ml). The combined organic layers were washed with brine (20 ml), dried and concentrated. The residue was chromatographed on silica using 9:1 ER-methanol as eluent to give the title compound as a foam (2 g).

Analysis Found: C, 66.3; H, 7.0; N, 3.3. $C_{23}H_{29}NO_4S$ requires: C, 66.5; H, 7.0; N, 3.4%.

INTERMEDIATE 8

[1α(Z),2β,3α,5α]-(±)-7-[3-Hydroxy-2-(4-morpholinyl)-5-[(2-phenylthien-4-yl)methoxy]cyclopentyl]-4-heptenoic acid To an intimate mixture of potassium t-butoxide (1.89 g) and (3-carboxypropyl) triphenylphosphonium bromide (3.62 g) under nitrogen was added dry THF (50 ml). The suspension formed was stirred for 30 min whereupon a solution of Intermediate 7 (1.75 g) in dry THF (10 ml) was added in one portion. Stirring was maintained for 1h whereupon water (40 ml) and $NaHCO_3$ solution (10 ml) were added and the mixture extracted with ER (3×50 ml). The extracts were discarded and the aqueous phase acidified to pH 6.5 with $KH_2PO_4$ solution and extracted with ER (3×75 ml). The combined ethereal extracts were washed with water (50 ml), brine (50 ml) and then dried. After evaporation the residue was chromatographed on silica using 4:1 ER-methanol as eluent to give the title compound as a foam (1.15 g).

Analysis Found: C, 66.8; H, 7.3; N, 3.0. $C_{27}H_{35}NO_5S$ requires: C, 66.8; H, 7.3; N, 2.9%.

INTERMEDIATE 9

4-Phenyl-2-thiophenemethanol

A stirred suspension of 4-phenyl-2-thiophenecarboxaldehyde (4.32 g) in absolute ethanol (85 ml) was cooled in an ice-bath and treated with NaBH$_4$ (1.06 g). After 20 min. the mixture was allowed to attain ambient temperature when stirring was continued for 6h. Saturated aqueous NH$_4$Cl (30 ml) was then carefully added to the vigorously stirred mixture, and the resulting suspension extracted with ER (2×200 ml). The combined extracts were dried (Na$_2$SO$_4$/K$_2$CO$_3$), filtered and evaporated to give the title compound (4.2 g) as crystals, m.p. 112°–113°.

INTERMEDIATE 10

2-(Bromomethyl)-4-phenylthiophene

A cooled, stirred suspension of Intermediate 9 (3.86 g) in dry CH$_2$Cl$_2$ (60 ml) was treated dropwise with a solution of PBr$_3$ (1.27 ml) in dry CH$_2$Cl$_2$ (20 ml), and stirring continued for 30 min. The mixture was treated with 8% aqueous NaHCO$_3$ (100 ml), stirred for 20 min., extracted with ER (1×150 ml, 1×50 ml), and the extracts dried (MgSO$_4$), filtered and evaporated to give the title compound (5.01 g) as a solid, m.p. 87°–88.5°.

INTERMEDIATE 11

4-(1,3-Dioxolan-2-yl)-2-phenylthiophene

A solution of 5-bromo-3-thiophenecarboxaldehyde (32.5 g) in benzene (500 ml) was treated with p-toluenesulphonic acid monohydrate (0.323 g) and ethylene glycol (21.1 g), and the mixture heated under reflux in a Dean and Stark apparatus until the theoretical volume of water had been removed. After cooling the mixture was washed with water, (2 x) then brine, dried, filtered and concentrated, and the residue distilled (b.p. 96°–100° at 0.4 mm) to give the title compound as an oil (24 g).

Analysis Found: C, 35.8; H, 3.0. $C_7H_7BrO_2S$ required: C, 35.7; H, 3.0%.

INTERMEDIATE 12

5-Phenyl-3-thiophenecarboxaldehyde

A solution of phenylmagnesium chloride in THF (82.94 ml, 2.39 M) was added to a stirred solution of ZnBr$_2$ (44.6 g) in dry THF (350 ml) under nitrogen. The mixture was stirred at room temperature for 15 min.

DIBAL (9.91 ml, 1 M) in hexane solution was added dropwise to a stirred mixture of triphenylphosphine (10.39 g) and nickel acetoacetonate (2.55 g) in dry THF (160 ml) under nitrogen. A solution of Intermediate 11 (23.3 g) in dry THF (150 ml) was added after 10 min. The solution containing the organozinc reagent was then added dropwise and the mixture was stirred for 1h.

2 N hydrochloric acid (400 ml) was added at 0° and the mixture was stirred at room temperature for 0.5h. The two layers were separated and the aqueous layer was extracted with ER (2×400 ml), washed with NaHCO$_3$ solution and brine and then dried. Solvent removal in vacuo gave a solid (32.8 g) which was chromatographed using 9:1 PE (b.p. 60°–80°)-EA or eluent to give the title compound (13.35 g), m.p. 64°–65° (from PE (b.p. 60°–80°)).

INTERMEDIATE 13

5-Phenyl-3-thiophenemethanol

A stirred solution of Intermediate 12 (12 g) in methanol (120 ml) was treated with NaBH$_4$ (1.82 g) at room temperature for 15 min. The mixture was cooled to 0° and treated with NH$_4$Cl solution (200 ml), followed by water (200 ml) and ER (400 ml). The ER extract was separated and the aqueous phase further extracted with ER (400 ml), washed with brine, dried, filtered and evaporated to afford the title compound as a solid (11.5 g), m.p. 92°–93°.

INTERMEDIATE 14

4-(Bromomethyl)-2-phenylthiophene

Intermediate 13 was converted into the title compound by the method for the preparation of Intermediate 10. TLC (ER) Rf 0.58.

EXAMPLE 1

[1α(Z),2β,5α]-(±)-7-[2-(4-Morpholinyl)-3-oxo-5-[(2-phenylthien-4-yl)methoxy]cyclopentyl]-4-heptenoic acid A solution of DMSO in dry toluene (1.46 ml, 1.41 M) was added dropwise to a solution of oxalyl chloride in dry toluene (1.8 ml, 1.15 M) at −70° under nitrogen and the mixture stirred for 15 min. Simultaneously, a solution of Intermediate 8 (0.4 g) in dry toluene (4 ml) was treated with a solution of triethylamine in dry toluene (1.13 ml, 0.8 M) followed by a solution of trimethylsilyl chloride in dry toluene (1.07 ml, 0.085 M). After stirring at room temperature for 10 min the mixture was added to the above prepared solution of activated DMSO and stirring continued for 30 min. Triethylamine (2 ml) in toluene (5 ml) was added and after a further 30 min the mixture was treated with 1 M aqueous KH$_2$PO$_4$ (20 ml) and extracted with ether (3×20 ml). The combined extracts were washed with water (50 ml), brine (30 ml) and then dried. After evaporation in vacuo the residue was chromatographed on silica using 2:1 EA-PE (b.p. 60°–80°) as eluent to give the title compound as a solid (0.27 g). Crystallisation from ER-isopentane at −10° gave material of m.p. 52°–55°. IR (CHBr$_3$) 3500, 1735, 1703 cm$^{-1}$.

EXAMPLE 2

[1α(Z),2β,5α]-(±)-7-[2-(4-Morpholinyl)-3-oxo-5-[(4-phenylthien-2-yl)methoxy]cyclopentyl]-4-heptenoic acid Prepared for Intermediate 5 using a similar procedure to that of Example 1. m.p. 86°–88°.

Analysis Found: C, 66.8; H, 6.8; N, 2.8. $C_{27}H_{33}NO_5S$ requires: C, 67.1; H, 6.9; N, 2.9%.

PHARMACEUTICAL EXAMPLES

Tablets

These may be prepared by direct compression or wet granulation. The direct compression method is preferred but may not be suitable in all cases as it is dependent upon the dose level and physical characteristics of the active ingredient.

| A. Direct Compression | mg/tablet |
|---|---|
| Active ingredient | 100.00 |
| Microcrystalline Cellulose B.P.C. | 298.00 |
| Magnesium Stearate | 2.00 |
| Compression Weight | 400.00 |

The active ingredient is sieved through a 250 m$^{-6}$ sieve, blended with the excipients and compressed using 10.0 mm punches. Tablets of other strengths may be prepared by altering the compression weight and using punches to suit.

| B. Wet Granulation | mg/tablet |
|---|---|
| Active ingredient | 100.00 |
| Lactose B.P. | 238.00 |
| Starch B.P. | 40.00 |
| Pregelatinised Maize Starch B.P. | 20.00 |
| Magnesium Stearate B.P. | 2.00 |
| Compressed Weight | 400.00 |

The active ingredient is sieved through a 250 m$^{-6}$ sieve and blended with the lactose, starch and pregelatinised starch. The mixed powders are moistened with purified water, granules are made, dried, screened and blended with the magnesium stearate. The lubricated granules are compressed into tablets as described for the direct compression formulae.

The tablets may be film coated with suitable film forming materials, e.g. methyl cellulose or hydroxylpropyl methyl cellulose using standard techniques. Alternatively the tablets may be sugar coated.

| Capsules | mg/capsule |
|---|---|
| Active ingredient | 100.00 |
| *STA-RX 1500 | 99.00 |
| Magnesium Stearate B.P. | 1.00 |
| Fill Weight | 200.00 mg |

*A form of directly compressible starch supplied by Colorcorn Ltd., Orpington, Kent.

The active ingredient is sieved through a 250 m$^{-6}$ sieve and blended with the other materials. The mix is filled into No. 2 hard gelatin capsules using a suitable filling machine. Other doses may be prepared by altering the fill weight and if necessary changing the capsule size to suit.

| Inhalation Cartridges | /cartridge |
|---|---|
| Active ingredient (micronised) | 3 mg |
| Lactose B.P. to | 25 mg |

The active ingredient is micronised so that the majority of the particles are between 1 m$^{-6}$ and 5 m$^{-6}$ in longest dimensions and none are greater than 10 m$^{-6}$. The active ingredient is then blended with the lactose and the mix is filled into No. 3 hard gelatin capsules using a suitable filling machine.

| Suspensions | mg/5 ml dose |
|---|---|
| Active ingredient | 100.0 |
| Aluminum monostearate | 75.0 |
| Sucrose (powdered) | 125.0 |
| Flavour } Color } | as required |
| Fractionated coconut oil to | 5.00 ml. |

The aluminium monostearate is dispersed in about 90% of the fractionated coconut oil. The resulting suspension is heated to 115° C. while stirring and then cooled. The flavour and colour are added and the active ingredient and sucrose are suitably dispersed. The suspension is made up to volume with the remaining fractionated coconut oil and mixed.

| Injection for Intravenous Administration | |
|---|---|
| Active ingredient | to mg |
| Suitable vehicle to | 5 ml. |

A sterile presentation of the active ingredient in an ampoule or vial together with an ampoule containing a suitable vehicle. The former may be prepared by (a) filling sterile material into vials under aseptic conditions (b) freeze drying a sterile solution of the active ingredient under aseptic conditions.

The vehicle may be (a) Water for Injections B.P. (b) Water for Injections B.P. containing: (1) Sodium chloride to adjust the tonicity of the solution and/or (2) buffer salts or dilute acid or alkali to facilitate solution of the active ingredient.

The vehicle is prepared, clarified and filled into appropriate sized ampoules sealed by fusion of the glass. The vehicle is sterilised by heating in an autoclave using one of the acceptable cycles.

We claim:

1. Compounds of the general formula (1)

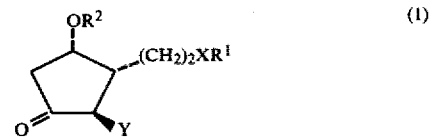

wherein
X is cis or trans —CH=CH—;
R$^1$ is straight or branched C$_{1-7}$ alkyl bearing as a terminal substituent —COOR$^3$ where R$^3$ is a hydrogen atom, C$_{1-6}$ alkyl or C$_{7-10}$ aralkyl;
Y represents a saturated heterocyclic amino group which has 5 to 8 ring members and (a) optionally contains in the ring —O—, —S—, —SO$_2$—, —NR$^4$ (where R$^4$ is a hydrogen atom, C$_{1-7}$ alkyl or aralkyl having a C$_{1-4}$ alkyl portion; and/or (b) is optionally substituted by one or more C$_{1-4}$ alkyl groups;
R$^2$ is C$_{1-5}$ alkyl substituted by thienyl or furanyl (the thienyl and furanyl groups being optionally substituted by C$_{1-6}$ alkyl, C$_{1-6}$ alkoxy, aryl or phenyl (C$_{1-3}$) alkyl or phenyl (C$_{1-3}$)-alkoxy (the aryl or phenyl group in each case being optionally substituted by C$_{1-3}$ alkyl, C$_{1-3}$ alkoxy or halogen), aryloxy, C$_{5-7}$ cycloalkyl, halogen, nitro or thienyl);
and the physiologically acceptable salts and the solvates thereof.

2. Compounds as claimed in claim 1 in which Y is morpholino, dioxothiamorpholino, homomorpholino, thiamorpholino or piperidino.

3. Compounds as claimed in claim 1 in which X is cis —CH=CH—.

4. Compounds as claimed in claim 1 in which $R^1$ is —$(CH_2)_2COOR^3$ where $R^3$ is a hydrogen atom or $C_{1-3}$ alkyl alkyl.

5. Compounds as claimed in claim 1 in which $R^2$ is phenylthienyl ($C_{1-3}$) alkyl.

6. Compounds as claimed in claim 1 in which:
X is cis —CH=CH—;
$R^1$ is —$(CH_2)_2COOH$;
Y is morpholino or piperidino;
$R^2$ is phenylthienyl ($C_{1-3}$) alkyl;
and the physiologically acceptable salts and solvates thereof.

7. Compounds as claimed in claim 1 in which the carbon atom carrying the —$(CH_2)_2XR^1$ group is in the R-configuration.

8. A pharmaceutical composition comprising an effective amount of a compound as claimed in claim 1 together with one or more pharmaceutical carriers.

* * * * *